United States Patent
Lang et al.

[11] Patent Number: 5,938,792
[45] Date of Patent: *Aug. 17, 1999

[54] PROCESS FOR DYEING KERATINOUS FIBERS WITH AMINOINDOLES AND OXIDATION DYE PRECURSORS AT BASIC PH'S AND DYEING AGENTS

[75] Inventors: Gerard Lang, Saint-Gratien; Alex Junino, Livry-Gargan; Jean Cotteret, Verneuil-sur-Seine; Alain Lagrange, Chatou, all of France

[73] Assignee: L'Oreal, Paris, France

[*] Notice: This patent is subject to a terminal disclaimer.

[21] Appl. No.: 08/889,896

[22] Filed: Jul. 8, 1997

Related U.S. Application Data

[62] Continuation of application No. 08/543,866, Oct. 19, 1995, abandoned, which is a continuation of application No. 08/137,019, filed as application No. PCT/FR92/00289, Mar. 30, 1992, abandoned.

[30] Foreign Application Priority Data

Apr. 18, 1991 [FR] France .................................. 91/04801

[51] Int. Cl.$^6$ ........................................................ A61K 7/13
[52] U.S. Cl. ........................... 8/409; 8/408; 8/410; 8/411; 8/412; 8/423
[58] Field of Search ................ 8/405, 406, 408, 8/409, 410, 411, 412, 423

[56] References Cited

U.S. PATENT DOCUMENTS

| | | | |
|---|---|---|---|
| 4,013,404 | 3/1977 | Parent et al. ................... | 8/11 |
| 4,776,857 | 10/1988 | Carroll et al. ................. | 8/423 |
| 5,053,053 | 10/1991 | Delabby et al. ............... | 8/423 |
| 5,112,360 | 5/1992 | Garoche et al. ............... | 8/406 |
| 5,143,518 | 9/1992 | Madrange et al. ............ | 8/405 |
| 5,254,135 | 10/1993 | Lang et al. .................... | 8/408 |
| 5,364,414 | 11/1994 | Lang et al. .................... | 8/423 |
| 5,752,982 | 5/1998 | Lang et al. .................... | 8/409 |

FOREIGN PATENT DOCUMENTS

| | | |
|---|---|---|
| 0271186 | 6/1988 | European Pat. Off. . |
| 0348280 | 12/1989 | European Pat. Off. . |
| 0414585 | 2/1991 | European Pat. Off. . |
| 0424261 | 4/1991 | European Pat. Off. . |
| 0425345 | 5/1991 | European Pat. Off. . |
| 0462883 | 12/1991 | European Pat. Off. . |
| 0465339 | 1/1992 | European Pat. Off. . |
| 0465340 | 1/1992 | European Pat. Off. . |
| 2626771 | 8/1989 | France . |
| 2205329 | 12/1988 | United Kingdom . |

*Primary Examiner*—Paul Lieberman
*Assistant Examiner*—Caroline D. Liott
*Attorney, Agent, or Firm*—Pillsbury Madison & Sutro LLP

[57] ABSTRACT

The invention relates to a process for dyeing keratinous fibres, which consists in applying to these fibres a composition containing, in a suitable medium for dyeing, at least one coupler of formula:

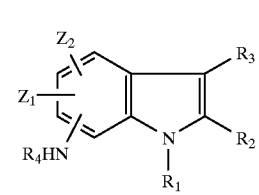

(I)

where
- $R_1$ denotes hydrogen or alkyl,
- $R_2$ and $R_3$ denote hydrogen, alkyl, COOR' where R' is alkyl or hydrogen,
- at least one of the groups $R_2$ and $R_3$ denoting hydrogen,
- $R_4$ denotes hydrogen, alkyl, hydroxyalkyl, polyhydroxyalkyl or aminoalkyl,
- $Z_1$ and $Z_2$ denote hydrogen, alkyl, hydroxyl, halogen, alkoxy,
- at least one of the groups $Z_1$ and $Z_2$ is other than hydrogen
  - at least one oxidation dye precursor,
    - at least one oxidizing agent, the pH of the composition applied to the fibres being higher than 7.

18 Claims, No Drawings

PROCESS FOR DYEING KERATINOUS FIBERS WITH AMINOINDOLES AND OXIDATION DYE PRECURSORS AT BASIC PH'S AND DYEING AGENTS

This is a continuation of application Ser. No. 08/543,866, filed on Oct. 19, 1995, now abandoned, which is a continuation of application Ser. No. 08/137,019, filed on Apr. 22, 1994, which was abandoned upon the filling hereof and was a 371 of PCT/PR92/00289 filed Mar. 30, 1992.

The present invention relates to a new process for dyeing keratinous fibers, in particular human keratinous fibers, using aminoindoles in combination with oxidation bases and an oxidizing agent in basic medium, to the compositions used during this process and to new aminoindole compounds.

It is known to dye keratinous fibers and in particular human hair with dye compositions containing, in alkaline medium, oxidation dye precursors and in particular p-phenylenediamines or ortho or para-aminophenols, usually called "oxidation bases".

It is also known that the shades obtained with these oxidation bases can be varied by using them in combination with couplers, also known as color modifiers, chosen especially from aromatic meta-diamines, meta-aminophenols and meta-diphenols.

The applicants have surprisingly just found that the use of certain compounds of the aminoindole type in combination with oxidation bases produces colors exhibiting an excellent dyeing power when this combination is applied to hair in the presence of an oxidizing agent and at basic pH.

The colors thus obtained exhibit an excellent tenacity to light, washing, perspiration and inclement weather.

The subject of the present invention is therefore a process for dyeing keratinous fibers, in particular human keratinous fibers such as hair, comprising the application to these fibers of a composition containing at least one aminoindole of formula (I) as defined below, of an oxidation dye precursor also called an oxidation base and of an oxidizing agent, at basic pH.

Another subject of the invention is a two-component dyeing agent in which one of the components comprises aminoindole and the oxidation dye precursor and the other the oxidizing agent, in quantities such that the mixture exhibits an acidic pH.

A further subject also consists of oxidation dyeing compositions containing an oxidation dye precursor and one of these particular compounds as coupler.

Another subject of the invention is the ready-for-use composition containing the various agents employed for the dyeing of hair in basic medium.

Other subjects of the invention will appear on reading the description and the examples which follow.

The process for dyeing keratinous fibers and in particular human keratinous fibres such as hair, in accordance with the invention, is essentially characterised in that there is applied to these fibers a composition containing, in a suitable medium for dyeing, at least one coupler corresponding to the formula:

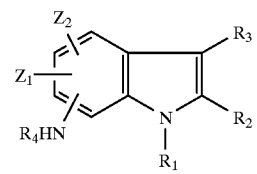

in which:
$R_1$ denotes hydrogen or an optionally branched $C_1$–$C_4$ alkyl group,
$R_2$ and $R_3$, independently of each other, denote a hydrogen atom, a $C_1$–$C_4$ alkyl group or a COOR' group, R' being a $C_1$–$C_4$ alkyl radical or a hydrogen atom,
at least one of the groups $R_2$ and $R_3$ denotes a hydrogen atom,
$R_4$ denotes a hydrogen atom, a $C_1$–$C_4$ alkyl group or a $C_1$–$C_4$ hydroxyalkyl, $C_2$–$C_4$ polyhydroxyalkyl or $C_1$–$C_6$ aminoalkyl group in which the amine may be optionally mono- or disubstituted by a $C_1$–$C_4$ alkyl,
it being possible for the —$NHR_4$ group to occupy positions 4, 6 or 7,
$Z_1$ and $Z_2$, which are identical or different, denote a hydrogen atom or a $C_1$–$C_4$ alkyl, hydroxyl, halogen or $C_1$–$C_4$ alkoxy group,
at least one of the groups $Z_1$ and $Z_2$ is other than hydrogen,
and the salts of all these compounds;
at least one oxidation dye precursor,
at least one oxidising agent,
the pH of the composition applied to the fibers being higher than 7.

The preferred compounds corresponding to the formula (I) and employed in accordance with the invention are the following:
(1) 4-methyl-6-aminoindole,
(2) 5-methyl-6-aminoindole,
(3) 7-methyl-4-aminoindole,
(4) 3-methyl-7-ethyl-6-aminoindole,
(5) 2-methyl-5-hydroxy-6-aminoindole,
(6) 5,7-dimethyl-6-aminoindole,
(7) 5,7-diethyl-6-aminoindole,
(8) 2-ethoxycarbonyl-5-methyl-7-aminoindole,
(9) 2-ethoxycarbonyl-5-chloro-7-aminoindole,
(10) 2-ethoxycarbonyl-5-ethoxy-7-aminoindole,
(11) 2-ethoxycarbonyl-5-methoxy-7-aminoindole,
(12) 5-methoxy-7-(4'-dimethylamino-1'-methylbutyl) aminoindole,
(13) 5-methoxy-7-(4'-dimethylaminobutyl)aminoindole,
(14) 5-methoxy-7-(4'-diethylamino-1'-methylbutyl) aminoindole,
(15) 5-fluoro-6-aminoindole,
(16) 5-fluoro-1-sec-butyl-6-aminoindole,
(17) 5-fluoro-1-n-propyl-6-aminoindole,
(18) 1-methyl-2-methoxycarbonyl-5-methoxy-6-aminoindole,
(19) 2-methoxycarbonyl-5-methoxy-6-aminoindole,
(20) 2-ethoxycarbonyl-5-methoxy-6-aminoindole,
(21) 2-carboxy-5-methoxy-6-aminoindole,
(22) 1,2-dimethyl-5-hydroxy-6-aminoindole,
(23) 2-methoxycarbonyl-4-methoxy-6-aminoindole.
(21) 2-carboxy 5-méthoxy 6-aminoindole,

(22) 1,2-diméthyl 5-hydroxy 6-aminoindole,
(23) 2-méthoxycarbonyl 4-méthoxy 6-aminoindole,
(24) 7-éthyl 4-aminoindole,
(25) 7-éthyl 6-aminoindole,
(26) 7-éthyl 6-N,β-hydroxyéthylaminoindole.

The salts are chosen more particularly from hydrochlorides or hydrobromides. The compounds (1) to (7) and, (24) to (26) can be prepared by reduction of the corresponding nitro derivatives. Some of these nitro derivatives are known according to the paper Bergman & Sand, Tetrahedron, Vol. 46, No. 17, pages 6085 to 6112, 1990. The nitro compounds not described in this paper can be obtained by the same process, that is to say by the action of a trialkyl orthoformate on a dialkyl or trialkyl-meta-nitroaniline (one of the alkyl groups being situated in a position ortho to the amino group and para to the nitro group), in the presence of p-toluenesulphonic acid, followed by a ring closure of the product obtained.

4-Methyl-6-nitroindole and 5-methyl-6-nitroindole are new.

The reduction of the nitro group is performed according to the conventional reduction processes such as, for example, by reduction with iron in acetic acid or with zinc in the presence of alcohol and of ammonium chloride, or else by catalytic hydrogenation under hydrogen pressure in the presence of a hydrogenation catalyst.

The reduction can also take place by hydrogen transfer with a transfer agent such as cyclohexene in the presence of a hydrogenation catalyst.

The hydrogenation catalyst may consist, for example, of palladium or rhodium on a support such as carbon.

In the case where $Z_1$ or $Z_2$=Cl, the reduction is preferably done with iron in acetic acid or with zinc in the presence of alcohol and of ammonium chloride.

The compounds of formula (I) in which $R_4$ is other than a hydrogen atom can be prepared by the following process.

The compound (I) can be obtained from the compound ($R_4$=H) by the methods for substitution of aromatic amines, according to the reaction scheme:

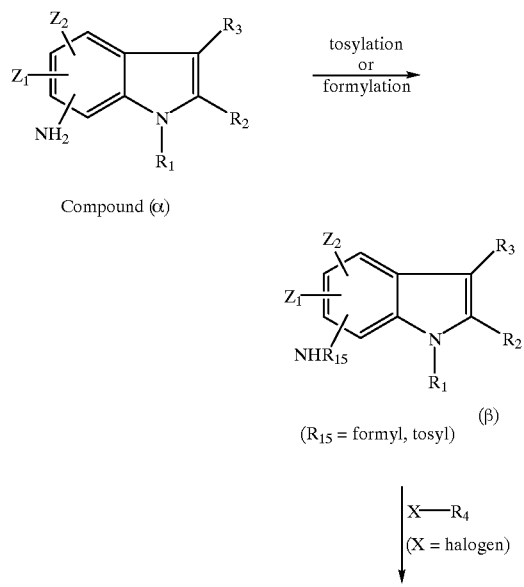

Compound (α)

(β)
($R_{15}$ = formyl, tosyl)

X—$R_4$
(X = halogen)

Compound (I) ←

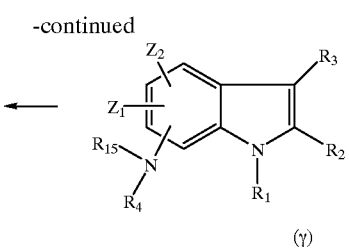

(γ)

The compound (β) is obtained by formylation or tosylation. In a second step the compound (β) is alkylated with the alkyl halide X-$R_4$ to obtain the compound (γ).

The expected product (I) is obtained by deformylation or detosylation of the compound (β), using conventional methods.

When $R_4$ denotes an alkyl group, the compound (I) can also be obtained by reduction of the compound (δ) with a metal hydride such as an alkali metal hydrobromide in the presence or absence of a Lewis acid, such as boron trifluoride etherate.

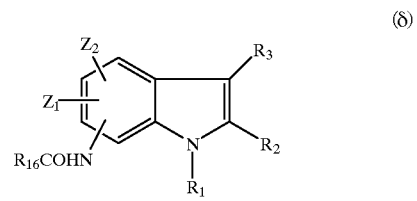

in which formula $R_{16}$ denotes a $C_1$–$C_3$ alkyl group or a hydrogen.

The compound (δ) being obtained from the compound (α) according to the known processes for obtaining alkylcarbonylamino groups.

Among the hydroxyalkylation methods there may be mentioned the action of β-chloroalkyl chloroformate on the compound (α), which, in a first step, makes it possible to obtain the corresponding β-chloroalkyl carbamate which, subjected to the action of a strong mineral base in a second step, makes it possible to obtain the compound (I) in the case of which the radical $R_4$ is a β-hydroxyalkyl radical.

The oxidation dye precursors or oxidation bases are known compounds which are not dyes themselves and which form a dye by a process of oxidative condensation, either with themselves or in the presence of a coupler or modifier. These compounds generally include an aromatic nucleus carrying functional groups consisting either of two amino groups or of an amino group and a hydroxyl group, these groups being in para or ortho position relative to each other.

The oxidation dye precursors of para type which are employed in accordance with the invention are chosen from para-phenylenediamines, so-called "double" bases, para-aminophenols and para heterocyclic precursors such as 2,5-diaminopyridine, 2-hydroxy-5-aminopyridine or 2,4,5,6-tetraaminopyrimidine.

Among para-phenylenediamines there may be mentioned the compounds corresponding to the formula (II):

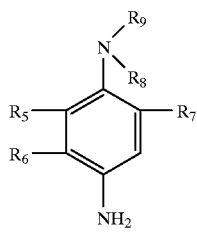

(II)

in which:

$R_5$, $R_6$ and $R_7$, which are identical or different, denote a hydrogen or halogen atom, an alkyl radical containing from 1 to 4 carbon atoms, an alkoxy radical containing from 1 to 4 carbon atoms, or a carboxyl, sulpho or hydroxyalkyl radical containing from 1 to 4 carbon atoms, $R_8$ and $R_9$, which are identical or different, denote a hydrogen atom or an alkyl, hydroxyalkyl, alkoxyalkyl, carbamylalkyl, aminoalkyl, mesylaminoalkyl, acetylaminoalkyl, ureidoalkyl, carbalkoxyaminoalkyl, piperidinoalkyl or morpholinoalkyl radical, these alkyl or alkoxy groups containing from 1 to 4 carbon atoms, or else $R_8$ and $R_9$, together with the nitrogen atom to which they are linked, form a piperidino or morpholino heterocyclic ring, provided that $R_5$ or $R_7$ denotes a hydrogen atom when $R_8$ and $R_9$ do not denote a hydrogen atom, and the salts of these compounds.

Among the particularly preferred compounds corresponding to the formula (II) there may be mentioned p-phenylenediamine, 2-methyl-p-phenylenediamine, methoxy-para-phenylenediamine, chloro-para-phenylenediamine, 2,6-dimethyl-para-phenylenediaminne, 2,5-dimethyl-para-phenylenediamine, 2,3-dimethyl-para-phenylenediamine, 2,6-diethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N -diethylaniline, N,N-di(β-hydroxyethyl)-para-phenylenediamine, 3-methyl-4-amino-N,N-di(β-hydroxyethyl)aniline, 3-chloro-4-amino-N,N-di(β-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl,β-piperidinoethyl)aniline, 3-methyl-4-amino-N,N-(ethyl,β-piperidinoethyl)aniline, 4-amino-N,N-(ethyl,β-morpholinoethyl)aniline, 3-methyl-4-amino-N,N-(ethyl,β-morpholinoethyl)aniline, 4-amino-N,N-(ethyl,β-acetylaminoethyl)aniline, 4-amino-N-(β-methoxyethyl) aniline, 3-methyl-4-amino-N,N-(ethyl,β-acetylaminoethyl) aniline, 4-amino-N,N-(ethyl,β-mesylaminoethyl)aniline, 3-methyl-4-amino-N,N-(ethyl,β-mesylaminoethyl)aniline, 4-amino-N,N-(ethyl,β-sulphoethyl)aniline, 3-methyl-4-amino-N,N-(ethyl,β-sulphoethyl)aniline, N-[(4'-amino) phenyl]morpholine, N-[(4'-amino)phenyl]piperidine, 2-hydroxyethyl-para-phenylenediamine, fluoro-para-phenylenediamine, carboxy-para-phenylenediamine, sulpho-para-phenylenediamine, 2-isopropyl-para-phenylenediamine, 2-n-propyl-para-phenylenediamine, 2-hydroxymethyl-para-phenylenediamine, N,N-dimethyl-3-methyl-para-phenylenediamine, N,N-(ethyl,β-hydroxy-ethyl)-para-phenylenediamine, N-(dihydroxypropyl)-para-phenylenediamine, N-4'-aminophenyl-p-phenylenediamine and N-phenyl-p-phenylenediamine.

These oxidation dye precursors of para type may be introduced into the dye composition either in the form of free base or in the form of salts such as in the form of hydrochloride, hydrobromide or sulphate.

The so-called double bases are bis-phenylenealkylenediamines, corresponding to the formula:

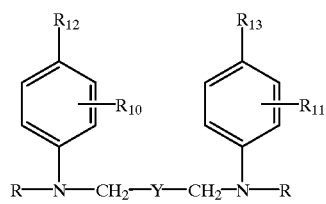

(III)

in which:

$R_{12}$ and $R_{13}$, which are identical or different, denote hydroxyl or $NHR_{14}$ groups, where $R_{14}$ denotes a hydrogen atom or a lower alkyl radical, $R_{10}$ and $R_{11}$, which are identical or different, denote either hydrogen atoms or halogen atoms or alkyl groups, R denotes a hydrogen atom or an alkyl, hydroxyalkyl or aminoalkyl group in which the amino residue may be substituted, Y denotes a radical taken from the group consisting of the following radicals:

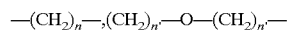

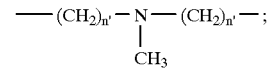

n being an integer between 0 and 8 and n' an integer between 0 and 4, it being possible for this base to be in the form of its addition salts with acids.

The alkyl or alkoxy radicals preferably denote a group containing 1 to 4 carbon atoms and especially methyl, ethyl, propyl, methoxy or ethoxy.

Among the compounds of formula (III), there may be mentioned N,N'-bis-(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl) tetramethylenediamine, N,N'-bis(4-methylaminophenyl) tetramethylenediamine and N,N'-bis(ethyl)-N,N'-bis(4'-amino-3'-methylphenyl)ethylenediamine.

Among p-aminophenols there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol, 2-methoxymethyl-4-aminophenol, 2-ethoxymethyl-4-aminophenol and 2-β-hydroxyethoxymethyl-4-aminophenol.

The oxidation dye precursors of ortho type are chosen from ortho-aminophenols such as 1-amino-2-hydroxybenzene, 6-methyl-1-hydroxy-2-aminobenzene, 4-methyl-1-amino-2-hydroxybenzene, 4-acetylamino-1-amino-2-hydroxybenzene and ortho-phenylene-diamines.

The oxidizing agent is preferably chosen from hydrogen peroxide, urea peroxide, alkali metal bromates and persalts such as perborates and persulphates. Hydrogen peroxide is particularly preferred.

The pH of the composition applied to the keratinous fibers, in particular hair, has a value higher than 7 and is preferably between 8 and 11. This pH is adjusted by the use of alkalifying agents which are well known in the field of dyeing of keratinous fibers and in particular of human hair, such as aqueous ammonia, alkali metal carbonates, alkanolamines such as mono-, di- or triethanolamine, and their derivatives or sodium or potassium hydroxides.

The compounds of formula (I) are present in the composition applied to the keratinous fibers in proportions which are preferably between 0.01 and 3.5% by weight relative to the total weight of the composition.

The compositions defined above and applied in the dyeing of keratinous fibers may also, in addition to the heterocyclic couplers of formula (I), contain other couplers which are known per se, such as meta-diphenols, meta-aminophenols, meta-phenylenediamines, meta-N-acylaminophenols, meta-ureidophenols, meta-carbalkoxyaminophenols, α-naphthol, couplers containing an active methylene group, such as diketonic compounds, pyrazolones, heterocyclic couplers or 4-hydroxyindole, 6-hydroxyindole or 7-hydroxyindole.

Among these couplers which may be employed in addition to the couplers of formula (I) there may be mentioned 2,4-dihydroxyphenoxyethanol, 2,4-dihydroxyanisole, meta-aminophenol, resorcinol, resorcinol monomethyl ether, 2-methylresorcinol, pyrocatechol, 2-methyl-5-N-(β-hydroxyethyl)aminophenol, 2-methyl-5-N-(β-mesylaminoethyl)aminophenol, 6-hydroxybenzomorpholine, 2,4-diaminoanisole, 2,4-diaminophenoxyethanol, 6-aminobenzomoroholine, [2-N-(β-hydroxyethyl)amino-4-amino]-phenoxyethanol, 2-amino-4-N-(β-hydroxyethyl) aminoanisole, (2,4-diamino)phenyl β,γ-dihydroxypropyl ether, 2,4-diaminophenoxyethylamine, 1,3-dimethoxy-2,4-diaminobenzene, 2-methyl-5-aminophenol, 2,6-dimethyl-3-aminophenol, 3,4-methylenedioxyphenol, 3,4-methylenedioxyaniline, 2-chlororesorcinol and their salts.

These compositions may also contain anionic, cationic, nonionic or amphoteric surface-active agents or mixtures thereof.

Among these surface-active agents there may be mentioned alkylbenzenesulphonates, alkylnaphthalenesulphonates, sulphates, ether sulphates and fatty alcohol sulphonates, quaternary ammonium salts such as trimethylcetylammonium bromide and cetylpyridinium bromide, optionally oxyethylenated fatty acid ethanolamides, polyoxyethylenated acids, alcohols or amines, polyglycerolated alcohols or alpha-diols, polyoxyethylenated or polyglycerolated alkylphenols and polyoxyethylenated alkyl sulphates.

The dye compositions are generally aqueous but may also contain organic solvents to solubilize compounds which might not be sufficiently soluble in water. Among these solvents there may be mentioned, by way of example, $C_2$–$C_4$ lower alkanols such as ethanol and isopropanol, glycerol, glycols or glycol ethers, such as 2-butoxyethanol, ethylene glycol, propylene glycol, diethylene glycol monoethyl ether and monomethyl ether, propylene glycol monoethyl ether and monomethyl ether and aromatic alcohols such as benzyl alcohol or phenoxyethanol, or mixtures of these solvents.

The composition applied to hair may also contain thickening agents which are chosen in particular from sodium alginate, gum arabic, cellulose derivatives such as methyl cellulose, hydroxyethyl cellulose, hydroxypropyl cellulose, hydroxymethyl cellulose or carboxymethyl cellulose, optionally crosslinked acrylic acid polymers or xanthan gum. It is also possible to employ inorganic thickening agents such as bentonite.

The composition may also contain antioxidant agents chosen in particular from sodium sulphite, thioglycolic acid, sodium bisulphite, dehydroascorbic acid and hydroquinone, as well as other cosmetically acceptable adjuvants when the composition is intended to be employed for dyeing human keratinous fibers, such as penetrating agents, sequestering agents, preserving agents, buffers, perfumes, and the like.

The composition applied to hair may be presented in various forms such as liquids, creams, gels, or in any other appropriate form for producing a hair dye. It may be packaged in an aerosol bottle in the presence of a propellent agent.

A further subject of the invention is the ready-for-use composition employed in the process defined above.

According to a preferred embodiment, the process comprises a preliminary stage consisting in storing in separate form, on the one hand, the composition containing, in a suitable medium for dyeing, the coupler corresponding to the formula (I) defined above and the oxidation dye precursors in the form of a component (A) and, on the other hand, a composition containing the oxidizing agent as defined above, in the form of a component (B), and in carrying out their extemporaneous mixing before applying this mixture to the keratinous fibers, as indicated above.

The composition applied to the keratinous fibers results from mixing of 10 to 90% of the component (A) with 90 to 10% of the component (B) containing an oxidizing agent.

A further subject of the invention is an agent for dyeing keratinous fibers, in particular hair, essentially characterised in that it comprises at least two components, one of the components consisting of the component (A) defined above and the other consisting of the component (B) also defined above, the pH of the components (A) and (B) being such that after mixing in proportions of 90 to 10% in the case of the component (A) and of 10 to 90% in the case of the component (B), the resulting composition has a pH higher than 7.

In this form of embodiment the component (A) which contains at least the coupler of formula (I) and an oxidation dye precursor may have a pH of between 8 and 12 and may be adjusted to the chosen value by means of alkalifying agents usually employed in dyeing keratinous fibers, such as aqueous ammonia, alkali metal carbonates, alkanolamines such as mono-, di- and triethanolamines, and their derivatives or sodium or potassium hydroxides.

This composition may contain the various other adjuvants referred to above, especially couplers other than aminoindole couplers corresponding to the formula (I) already mentioned above.

All of the oxidation dye precursors and the couplers are present in proportions which are preferably between 0.05 and 7% by weight relative to the total weight of the component (A). The concentration of compounds of formula (I) may vary between 0.012 and 4% by weight relative to the total weight of the component (A).

The surface-active agents are present in the component (A) in proportions of 0.1 to 55% by weight. When the mixture contains solvents in addition to water, these are present in proportions of between 0.5 and 40% by weight and in particular between 5 and 30% by weight relative to the total weight of the component (A). The thickening agents are preferably present in proportions of between 0.1 and 5% and in particular between 0.2 and 3% by weight. The antioxidant agents referred to above are preferably present in the component (A) in proportions of between 0.02 and 1.5% by weight relative to the total weight of the component (A).

It may be presented in the form of more or less thickened liquid, or of milk or gel.

This two-component dyeing agent may be packaged in a multicompartment device or dyeing kit, or any other packaging system with a number of compartments one of which contains the component (A) and the second compartment contains the component (B), it being possible for these devices to be provided with a means allowing the desired mixture to be delivered onto the hair, such as the devices described in the U.S. Pat. No. 4,823,985.

A further subject of the invention is the use, as couplers, of aminoindoles corresponding to the formula (I) for the dyeing of keratinous fibers in basic medium, in combination with oxidation dye precursors.

The dyeing process of the invention consists in applying the mixture obtained to the hair, in leaving it in place for 3 to 40 minutes and then in rinsing the hair and possibly shampooing it.

It is also possible, in accordance with the invention, to apply separately a composition containing the coupler of formula (I), the oxidation dye precursor and the oxidizing agent, so that the mixture formed in situ at the fibers has a pH higher than 7, as defined above.

The examples which follow are intended to illustrate the present invention without, however, being limiting in nature.

EXAMPLE OF PREPARATION 1

Synthesis of 4-Methyl-6-Aminoindole

1) SYNTHESIS OF 2,3-DIMETHYL-5-NITROANILINE 363 g of 2,3-xylidine are run into 1.8 of pure sulphuric acid while the temperature is kept at 40° C. To this solution, cooled to 12° C., a sulphonitric mixture (132 ml of nitric acid (d=1.52) and 180 ml of pure sulphuric acid) is added dropwise over 1 hour, the temperature not exceeding 15° C. After 15 minutes the mixture is poured onto 6 kg of ice with stirring.

The beige sulphate precipitate is filtered off, washed twice with 0.5 l of water and then three times with 0.5 l of acetone. The precipitate is slurried with 0.5 l of acetone, made alkaline with aqueous ammonia and then diluted with 1.5 l of iced water. The yellow precipitate is filtered off, washed with water and then dried. A yellow solid is obtained, which has the following characteristics:

Melting point: 110° C.

| Elemental analysis for $C_8H_{10}N_2O_2$ | | | | |
|---|---|---|---|---|
|  | C | H | N | O |
| Calculated | 57.83 | 6.02 | 16.87 | 19.28 |
| Found | 57.91 | 6.03 | 16.78 | 19.20 |

2) SYNTHESIS OF METHYL N-(2,3-DIMETHYL-5-NITROPHENYL)FORMIMIDATE 66.4 g of 2,3-dimethyl-5-nitroaniline, 0.4 l of trimethyl orthoformate and 1.6 g of para-toluenesulphonic acid are mixed and heated to reflux for 3 hours.

The mixture is poured onto 1 kg of ice, the precipitate is filtered off and is then washed twice with 0.5 l of water. The precipitate is redissolved in 0.2 l of ethyl acetate and filtered hot. The solid obtained after cooling is filtered off, washed with petroleum ether and dried.

Crystallization from isopropyl ether produces white crystals which have the following characteristics:

Melting point: 108° C.

| Elemental analysis for $C_{10}H_{12}N_2O_3$ | | | | |
|---|---|---|---|---|
|  | C | H | N | O |
| Calculated | 57.69 | 5.81 | 13.45 | 23.05 |
| Found | 57.74 | 5.84 | 13.39 | 23.25 |

3) SYNTHESIS OF 4-METHYL-6-NITROINDOLE

A solution of 31 g of potassium ethoxylate, 51 ml of ethyl oxalate and 0.25 l of dimethylformamide is added to a solution of methyl N-(2,3-dimethyl-5-nitrophenyl) formimidate (52 g) in 0.37 l of dimethylformamide. The temperature of the mixture is raised to 40° C. for 3 hours. The precipitate is filtered off and washed with water. The precipitate is taken up in hot isopropyl ether and then filtration is carried out.

The filtrate is evaporated and then subjected to chromatography on silica (eluent: 9/1 heptane/ethyl acetate). A yellow solid is obtained which has the following characteristics:

Melting point: 145° C.

| Elemental analysis for $C_9H_8N_2O_2$ | | | | |
|---|---|---|---|---|
|  | C | H | N | O |
| Calculated | 61.36 | 4.58 | 15.90 | 18.16 |
| Found | 61.30 | 4.58 | 15.88 | 18.20 |

4 SYNTHESIS OF 4-METHYL-6-AMINOINDOLE 4.3 g of nitro derivative prepared in stage 3, 20 ml of ethanol, 9 ml of cyclohexene, 3 ml of water and 2.2 g of 10% palladium on-carbon are mixed and are then heated to reflux for 2 hours.

The mixture is filtered hot, the catalyst is washed with alcohol, the filtrate is evaporated under vacuum. The precipitate is taken up in isopropyl ether, treated with vegetable charcoal and then filtered on celite.

After evaporation of the filtrate a beige solid is obtained which has the following characteristics:

Melting point: 102° C.

| Elemental analysis for $C_8H_{10}N_2$ | | | |
|---|---|---|---|
|  | C | H | N |
| Calculated | 73.97 | 6.85 | 19.18 |
| Found | 73.84 | 6.99 | 19.06 |

EXAMPLE OF PREPARATION 2

Synthesis of 4-Amino-7-Methylindole

The same reduction process from point 4 of Example 1 is employed, 4-nitro-7-methylindole being employed instead of 4-methyl-6-nitroindole.

A pale yellow solid is obtained which has the following characteristics:

Melting point: 131° C.

| Elemental analysis for $C_8H_{10}N_2$ | | | |
|---|---|---|---|
| | C | H | N |
| Calculated | 73.97 | 6.85 | 19.18 |
| Found | 73.95 | 6.94 | 19.11 |

EXAMPLE OF PREPARATION 3

Synthesis of 3-Methyl-6-Amino-7-Ethylindole

A mixture of 0.5 l of 96° ethanol, 0.5 l of glacial acetic acid and 100 g of hydrogen-reduced pure iron is heated to 90° C. 51 g of 3-methyl-6-nitro-7-ethylindole are added in portions over 15 minutes.

After 2 hours at 95° C. the ferric sludge is filtered off and the filtrate is cooled and diluted with three volumes of water. It is extracted with three times 0.5 l of ethyl acetate, the organic phases are washed, dried and evaporated. The residue is taken up in ethyl acetate, treated with vegetable charcoal, filtered and cooled.

The light beige precipitate is filtered off and washed with ethyl acetate. The solid is dissolved in 0.1 l of water and made alkaline with aqueous ammonia; an oil precipitates and then solidifies. The precipitate is filtered off and then washed to neutrality and then dried. A white solid is obtained which has the following characteristics:

Melting point: 106° C.

| Elemental analysis for $C_{11}H_{14}N_2$ | | | |
|---|---|---|---|
| | C | H | N |
| Calculated | 75.82 | 8.10 | 16.08 |
| Found | 76.01 | 8.10 | 16.06 |

PREPARATION EXAMPLE 4

Synthesis of 6-Nitro 7-Ethylindole
A/PREPARATION OF 7-ETHYLINDOLINE

A solution of 145 g of 7-ethylindole in 1.45 l of dimethoxyethane was prepared. Under nitrogen atmosphere, 49.6 a of sodium borohdride then 854 g of trichloroacetic acid were added under stirring during 1 hour, the reaction temperature being maintained at 20° C. with a carbon dioxide ice bath.

After 2 hours of stirring at ambiant temperature, the reaction mixture was poured under stirring in 2 l of 15% iced soda. 2 liters of water were added, then the aqueous phase was extracted with three times 0.4 l of isopropylic ether. The organic phases were washed, dried on sodium sulphate, then filtered. The filtrate was evapored for giving 150 g of oil (quantitative yield).

B/SYNTHESIS OF 6-NITRO 7-ETHYLINDOLINE a) 147 g of 7-ethylindoline as priorly prepared were poured in 0.45 of sulphuric acid at 98% by maintaining the temperature at 10° C. 42 ml of nitric acid at 100% were mixed to 120 ml of sulphuric acid at 98%. The sulphonitric mixture was poured dropwise for 1 hour by maintaining the temperature of reaction under 5° C. After 1 hour at this temperature, 4 kg of ice were poured. The reaction mixture was neutralized with concentrated ammonia under stirring, by maintaining the temperature at 10° C. The aqueous phase was extracted with 3 times 0.4 l of ethylacetate. The organic phases were washed, dried on sodium sulphate then evaporated.

b) The oil thus obtained was dissolved in 0.3 l of chlorhydric acid 12 N; a precipitate appeared and was drained. This solid was washed with ethanol and then with petroleum ether. The solid was taken up in iced water. Then the solution was brought to a basic pH with concentrated ammonia. A yellow precipitate was formed. It was drained, washed with water und dried under vacuum.

c) The solid was dissolved in 0.6 l of isopropylic ether, then 30 g of vegetable charcoal CECA L25 and 10 g of sodium sulphate were added. After filtration, the organic phase was dry evaporated. The orange oil was poured in 0.3 l of petroleum ether. The orange precipitate was drained and dried.

82 g of 6-nitro 7-ethylindole were obtained.

Melting point: 50° C.

Yield: 43%

C/PREPARATION OF 6-AMINO 7-ETHYLINDOLE 38.4 g of 6-nitro 7-ethylindoline were dissolved in 120 ml of absolute ethanol to which were added 19.2 g of palladium on charcoal at 10% (moisture 50%) and then heated to reflux for 2 hours.

The catalyst was filtered, washed with 100 ml of ethanol and the organic phases were evaporated under vacuum. The dry extract was taken up in 0.4 l of isoprolylic ether by refluxing with 3 g of vegetal charcoal. The organic phases were filtered, dried on sodium sulphate then dry evaporated. The solid was crystallized in 40 ml of isopropylic ether. The white crystal were drained, dried for obtaining 25 g Melting point: 108° C.

Yield: 78%

PREPARATION EXAMPLE 5

Synthesis of 4-Amino 7-Ethylindole
A/SYNTHESE OF 4-NITRO 7-ETHYLINDOLINE a) 147 g of 7-ethylindoline as priorly prepared were poured in 0.45 of sulphuric acid at 98%, by maintaining the temperature at 10° C. 42 ml of nitric acid at 100% were mixed to 120 ml of sulphuric acid at 98%. The sulphonitric mixture was poured dropwise for 1 hour by maintaining the temperature of reaction under 5° C. After 1 hour at this temperature, 4 kg of ice were poured. The reaction mixture was neutralized with concentrated ammonia under stirring, by maintaining the temperature at 10° C. The aqueous phase was extracted with 3 times 0.4 l of ethylacetate. The organic phases were washed, dried on sodium sulphate their evaporated.

b) The oil has obtained was dissolved in 0.3 l of chlorhydric acid 12 N; a precipitate appeared and was drained. This solid was washed with ethanol and then with petroleum ether. The solid was taken up in iced water. Then the solution was brought to a basic pH with concentrated ammonia. A yellow precipitate was formed. It was drained, washed with water und dried under vaccuum.

c) The chlorhydric phase obtained in b) was diluted by 0.5 kg of ice, then brought to a basic pH with concentrated ammonia. The precipitate obtained was drained, washed with water, washed with 2 times 60 ml of isopropylic ether and then dried Yield: 15%

Melting Point: 68° C.

B/PREPARATION OF 4-AMINO 7-ETHYLINDOLE 4-nitro 7-ethylindoline was reduced in the same manner than 6-nitro 7-ethylindoline. 6 g of indole recrystallized from a ethylacetate/isopropylic ether (⅓) mixture were obtained.

Melting point: 123° C.

Yield: 75%

PREPARATION EXAMPLE 6

Preparation of 6-(Betachloroethylurethan)-7-Ethylindole)

8 g of betachloroformiate were poured in a suspension of 8 g of 6-amino 7-ethylindole, 5.5 g of calcium carbonate in 24 ml of dioxane at reflux for 30 minutes. The mixture was poured on ice, then acidified. The precipitate was drained, washed with water then dried 13 g of white product were obtained Melting point: 132° C.

Yield: 98%

Preparation of 3-(7-Ethyl-1H-Indol-6-yl) Oxazolidin)-2-One

A mixture of 8 g of the above prepared urethan, 8 ml of 96° ethanol and 24 ml of 4 N soda was refluxed for 15 minutes. The mixture was poured on ice; the precipitate was drained, washed with water, with alcohol then with petroleum ether. After drying, 6.6 g were obtained.

Melting point: 248° C.

Yield: 96%

PREPARATION EXAMPLE 8

Preparation of 7-Ethyl, 6- N, β-Hydroxyethylaminoindole 12.2 g of oxazolidone as priorly prepared at 50° C. were added to a mixture of 31.5 g of potassium hydroxyde, 8 ml of water, 70 ml of ethanol. After 20 minutes at reflux, 400 g of ice were poured, the mixture was brought to a pH 5 with acetic acid. Ammonia was added until a pH 7.5–8. A white precitate was obtained, then washed with water and dried. The extraction of mother liquor gave a supplementary amount of 1.6 g. The whole content was crystallized in a ethylacetate/isopropylic ether (⅓). 8.9 g were obtained Melting point 105° C.

Yield: 82%

EXAMPLE OF DYEING 1

The following dyeing mixture is prepared:

| | | |
|---|---|---|
| 4-Methyl-6-aminoindole | 0.365 | g |
| para-Phenylenediamine | 0.27 | g |
| Nonylphenol oxyethylenated with 4 moles of ethylene oxide, sold under the name Cemulsol NP 4 by Rhone-Poulenc | 12.0 | g |
| Nonylphenol oxyethylenated with 9 moles of ethylene oxide, sold under the name Cemulsol NP 9 by Rhone Poulenc | 15.0 | g |
| Oleyl alcohol polyglycerolated with 2 moles of glycerol | 1.5 | g |
| Oleyl alcohol polyglycerolated with 4 moles of glycerol | 1.5 | g |
| Propylene glycol | 6.0 | g |
| Ethylenediaminetetraacetic acid sold under the name Trilon B | 0.12 | g |
| 22° Béaqueous ammonia | 11.0 | g |
| Water | q.s. 100.0 | g |
| pH = 9.8 | | |

90 g of 20-volume aqueous hydrogen peroxide are added at the time of use. The mixture, the pH of which is 9.7, is applied to natural hair for 30 minutes at 30° C.; after shampooing and rinsing it gives it a coppery chestnut color.

EXAMPLE OF DYEING 2

The following dyeing mixture is prepared:

| | | |
|---|---|---|
| 3-Methyl-7-ethyl-6-aminoindole | 0.435 | g |
| N,N-Di(β-hydroxyethyl)-para-phenylenediamine sulphate | 0.672 | g |
| 2-Butoxyethanol | 10.0 | g |
| Cetylstearyl alcohol sold under the name Alfol C 16/18 by Condea | 8.0 | g |
| Sodium cetyl stearyl sulphate sold under the name Lanette E Wax by Henkel | 0.5 | g |
| Ethoxylated castor oil sold under the name Cemulsol B by Rhone Poulenc | 1.0 | g |
| Oleoyl diethanolamide | 1.5 | g |
| Pentasodium salt of diethylenetriamine-pentaacetic acid, sold under the name Masquol DTPA by Protex | 2.5 | g |
| 22° Béaqueous ammonia | 11.0 | g |
| Water | q.s. 100.0 | g |
| pH = 10 | | |

100 g of 20-volume aqueous hydrogen peroxide are added at the time of use. The mixture, the pH of which is 9.7, is applied to natural hair for 25 minutes at 30° C.; after shampooing and rinsing it gives it a grey bronze color.

EXAMPLE OF DYEING 3

The following dyeing mixture is prepared:

| | |
|---|---|
| 2-Methyl-5-hydroxy-6-aminoindole | 0.405 g |
| para-Aminophenol | 0.272 g |
| Cetylstearyl alcohol sold under the name Alfol C 16/18 by Condea | 19.0 g |
| 2-Octyldodecanol sold under the name Eutanol G by Henkel | 4.5 g |
| Cetylstearyl alcohol containing 15 moles of ethylene oxide, sold under the name Mergital C.S. by Henkel | 2.5 g |
| Ammonium lauryl sulphate | 10.0 g |
| Cationic polymer containing the following repeat unit: | 4.0 g |

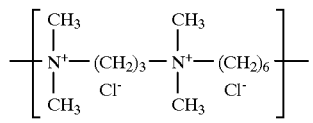

| | |
|---|---|
| Benzyl alcohol | 2.0 g |
| 22° Béaqueous ammonia | 11.0 g |
| Ethylenediaminetetraacetic acid sold under the name Trilon B | 1.0 g |
| 35° Bésodium bisulphite solution | 1.2 g |
| Water | q.s. 100.0 g |
| pH = 10.3 | |

80 g of 20-volume aqueous hydrogen peroxide are added at the time of use. The mixture, the pH of which is 9.4, is applied to bleached hair for 20 minutes at 30° C.; after shampooing and rinsing it gives it a dark beige color.

We claim:

1. A one-step oxidation process for dyeing human keratinous fibers comprising applying to said fibers under basic conditions a composition comprising, in a medium suitable for dyeing said fibers, (a) a coupler having the formula

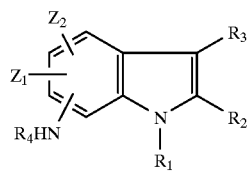

wherein $R_1$ represent hydrogen or a linear or branched $C_1$–$C_4$ alkyl, $R_2$ and $R_3$, each independently, represent hydrogen, $C_1$–$C_4$ alkyl or COOR' wherein R' represents $C_1$–$C_4$ alkyl or hydrogen, at least one of $R_2$ and $R_3$ represents hydrogen, $R_4$ represents hydrogen, $C_1$–$C_4$ alkyl, $C_1$–$C_4$ hydroxyalkyl, $C_2$–$C_4$ polyhydroxyalkyl or $C_1$–$C_6$ aminoalkyl wherein the amino function is optionally mono- or disubstituted by $C_1$–$C_4$ alkyl, the said —$NHR_4$ group occupying position 4, 6 or 7, $Z_1$ and $Z_2$, each independently, represent hydrogen, $C_1$–$C_4$ alkyl, hydroxyl, halogen or $C_1$–$C_4$ alkoxy, at least one of said $Z_1$ and $Z_2$ being other than hydrogen, and a salt of said compound of formula (I) in a sufficient amount;

(b) at least one oxidation dye precursor in a sufficient amount;

(c) at least one oxidation agent selected from the group consisting of hydrogen peroxide, urea peroxide, and alkali metal bromates, said at least one oxidation agent being present in an amount sufficient to develop coloration of said coupler and said oxidation dye precursor applied to said fibers, the pH of said composition applied to said fibers being greater than 7.

2. The process of claim 1 wherein said compound of formula (I) is selected from the group consisting of 4-methyl-6-aminoindole,
5-methyl-6-aminoindole,
7-methyl-4-aminoindole,
3-methyl-7-ethyl-6-aminoindole,
2-methyl-5-hydroxy-6-aminoindole,
5,7-dimethyl-6-aminoindole,
5,7-diethyl-6-aminoindole,
2-ethoxycarbonyl-5-methyl-7-aminoindole,
2-ethoxycarbonyl-5-chloro-7-aminoindole,
2-ethoxycarbonyl-5-ethoxy-7-aminoindole,
2-ethoxycarbonyl-5-methoxy-7-aminoindole,
5-methoxy-7-(4'-dimethylamino-1'-methylbutyl)-aminoindole,
5-methoxy-7-(4'-dimethylaminobutyl)aminoindole,
5-methoxy-7-(4'-diethylamino-1'-methylbutyl)aminoindole,
5-fluoro-6-aminoindole,
5-fluoro-1-sec-butyl-6-aminoindole,
5-fluoro-1-n-propyl-6-aminoindole,
1-methyl-2-methoxycarbonyl-5-methoxy-6-aminoindole,
2-methoxycarbonyl-5-methoxy-6-aminoindole,
2-ethoxycarbonyl-5-methoxy-6-aminoindole,
2-carboxy-5-methoxy-6-aminoindole,
1,2-dimethyl-5-hydroxy-6-aminoindole,
2-methoxycarbonyl-4-methoxy-6-aminoindole,
7-ethyl-4-aminoindole,
7-ethyl-6-aminoindole,
7-ethyl-6-N,β-hydroxyethylaminoindole, and the salts of said compounds.

3. The process of claim 1 wherein said oxidation dye precursor is selected from the group consisting of a compound having the formula

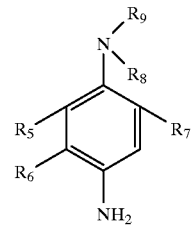

wherein $R_5$, $R_6$ and $R_7$, each independently, represent hydrogen, halogen, alkyl containing 1 to 4 carbon atoms, alkoxy containing 1 to 4 carbon atoms, or a carboxyl, sulpho or hydroxyalkyl radical containing 1 to 4 carbon atoms, $R_8$ and $R_9$, each independently, represent hydrogen, alkyl, hydroxyalkyl, alkoxyalkyl, carbamylalkyl, aminoalkyl, mesylaminoalkyl, acetylaminoalkyl, ureidoalkyl, carbalkoxyaminoalkyl, piperidinoalkyl, or morpholinoalkyl, wherein said alkyl or alkoxy groups contain from 1 to 4 carbon atoms, or $R_8$ and $R_9$, together with the nitrogen atom to which they are linked, form a piperidino or morpholino heterocyclic ring, provided that $R_5$ or $R_7$ represents hydrogen when $R_8$ and $R_9$ do not represent hydrogen, and the salt of said compound.

4. The process of claim 3 wherein said compound of formula (II) is selected from the group consisting of p-phenylenediamine,
2-methyl-p-phenylenediamine,
methoxy-para-phenylenediamine,
chloro-para-phenylenediamine,
2,6-dimethyl-para-phenylenediamine,
2,5-dimethyl-para-phenylenediamine,
2,3-dimethyl-para-phenylenediamine,
2,6-diethyl-para-phenylenediamine,
2-methyl-5-methoxy-para-phenylenediamine,
2,6-dimethyl-5-methoxy-para-phenylenediamine,
N,N-dimethyl-para-phenylenediamine,
3-methyl-4-amino-N,N-diethylaniline,
N,N-di(β-hydroxyethyl)-para-phenylenediamine,
3-methyl-4-amino-N,N-di(β-hydroxyethyl)aniline,
3-chloro-4-amino-N,N-di(β-hydroxyethyl)aniline,
4-amino-N,N-(ethyl,carbamylmethyl)aniline,
3-methyl-4-amino-N,N-(ethyl,carbamylmethyl)aniline,
4-amino-N,N-(ethyl,β-piperidinoethyl)aniline,
3-methyl-4-amino-N,N-(ethyl,β-piperidinoethyl)aniline,
4-amino-N,N-(ethyl,β-morpholinoethyl)aniline,
3-methyl-4-amino-N,N-(ethyl,β-morpholinoethyl)aniline, 4-amino-N,N-(ethyl,β-acetylaminoethyl)aniline,
4-amino-N-(β-methoxyethyl)aniline,
3-methyl-4-amino-N,N-(ethyl,β-acetylaminoethyl) aniline,
4-amino-N,N-(ethyl,β-mesylaminoethyl)aniline,
3-methyl-4-amino-N,N-(ethyl,β-mesylaminoethyl) aniline,
4-amino-N,N-(ethyl,β-sulphoethyl)aniline,
3-methyl-4-amino-N,N-(ethyl,β-sulphoethyl)aniline,
N-[(4'-amino)phenyl]morpholine,
N-[(4'-amino)phenyl]piperidine,
2-hydroxyethyl-para-phenylenediamine,
fluoro-para-phenylenediamine,
carboxy-para-phenylenediamine,
sulpho-para-phenylenediamine,
2-isopropyl-para-phenylenediamine,
2-n-propyl-para-phenylenediamine,
2-hydroxymethyl-para-phenylenediamine,
N,N-dimethyl-3-methyl-para-phenylenediamine,
N,N-(ethyl,β-hydroxyethyl)-para-phenylenediamine,
N-(dihydroxypropyl)-para-phenylenediamine,
N-4'-aminophenyl-p-phenylenediamine and
N-phenyl-p-phenylenediamine,
in the form of free base or salts.

5. The process of claim 3 wherein said oxidation dye precursor is selected from the group consisting of p-aminophenols chosen from
p-aminophenol,
2-methyl-4-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
2-hydroxyethyl-4-aminophenol,
2-(β-hydroxyethyl)-4-aminophenol,
2-methoxy-4-aminophenol,
3-methoxy-4-aminophenol,
2,5-dimethyl-4-aminophenol,
2-methoxymethyl-4-aminophenol,
2-ethoxymethyl-4-aminophenol and
2-β-hydroxyethoxymethyl-4-aminophenol.

6. The process of claim 3 wherein said oxidation dye precursor is selected from the group consisting of a bisphenylalkylenediamine of the formula:

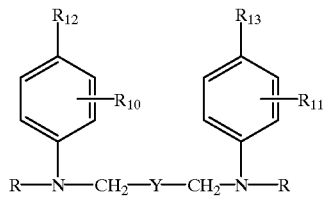

(III)

wherein
R$_{12}$ and R$_{13}$, each independently, represent hydroxyl or NHR$_{14}$ wherein R$_{14}$ represents hydrogen or lower alkyl, R$_{10}$ and R$_{11}$, each independently, represent hydrogen, halogen or alkyl,
R represents hydrogen, alkyl, hydroxyalkyl or aminoalkyl,
Y represents a member selected from the group consisting of —(CH$_2$)$_n$—, —(CH$_2$)$_{n'}$—O—(CH$_2$)$_{n'}$—, —(CH$_2$)$_{n'}$—CHOH—(CH$_2$)$_{n'}$, and $$—(CH_2)_{n'}—\underset{\underset{CH_3}{|}}{N}—(CH_2)_{n'}—,$$

n being an integer ranging from 0 to 8 and n' being an integer ranging from 0 to 4, and
an acid addition salt thereof.

7. The process of claim 6 wherein said phenylalkylenediamine is selected from the group consisting of
N,N'-bis-(β-hydroxyethyl)-N,N'-bis(4'-aminophenyl)-1,3-diamino-2-propanol,
N,N'-bis(β-hydroxyethyl)-N,N'-bis(4'-aminophenyl) ethylenediamine,
N,N'-bis(4-aminophenyl)tetramethylenediamine,
N,N'-bis(β-hydroxyethyl)-N,N'-bis(4-aminophenyl) tetramethylenediamine,
N,N'-bis(4-methylaminophenyl)tetramethylenediamine and
N,N'-bis(ethyl)-N,N'-bis(4'-amino-3'-methylphenyl) ethylenediamine.

8. The process of claim 1 wherein said oxidation dye precursor is selected from the group consisting of an ortho-aminophenol and an ortho-phenylenediamine.

9. The process of claim 1 wherein the pH of said composition applied to said keratinous fibers is between 8 and 11.

10. The process of claim 1 wherein said composition for dyeing human keratinous fibers also contains an additional coupler other than the said coupler (a), said additional coupler selected from the group consisting of a meta-diphenol, a meta-aminophenol, a meta-phenylenediamine, a meta-N-acylaminophenol, a meta-ureidophenol, a meta-carbalkoxyaminophenol, α-naphthol, a coupler containing an active methylene group selected from the group consisting of a diketonic compound, pyrazolone, a heterocyclic coupler, 4-hydroxyindole, 6-hydroxyindole and 7-hydroxyindole.

11. The process of claim 10 wherein said additional coupler is selected from the group consisting of
2,4-dihydroxyphenoxyethanol,
2,4-dihydroxyanisole,
meta-aminophenol,
resorcinol,
resorcinol monomethyl ether,
2-methyl-resorcinol,
pyrocatechol,
2-methyl-5-N-(β-hydroxyethyl)aminophenol,
2-methyl-5-N-(β-mesylaminoethyl)aminophenol,
6-hydroxybenzomorpholine,
2,4-diaminoanisole,
2,4-diaminophenoxyethanol,
6-aminobenzomorpholine,
[2-N-(β-hydroxyethyl)amino-4-amino]-phenoxyethanol,
2-amino-4-N-(β-hydroxyethyl)aminoanisole, (2,4-diamino)-phenyl-β,γ-dihydroxypropyl ether,
2,4-diaminophenoxyethylamine,
1,3-dimethoxy-2,4-diaminobenzene,
2-methyl-5-aminophenol,
2,6-dimethyl-3-aminophenol,
3,4-methylenedioxyphenol,
3,4-methylenedioxyaniline,
2-chlororesorcinol and
a salt thereof.

12. The process of claim 1 wherein said composition also contains an anionic, cationic, nonionic or amphoteric surface active agent or a mixture thereof, a thickening agent or an antioxidant agent.

13. The process of claim 1 wherein said medium suitable for dyeing said fibers comprises water or a mixture of water and a solvent, said solvent selected from the group consisting of a $C_2$–$C_4$ lower alkanol, glycerol, a glycol, an ether, an aromatic alcohol, and a mixture thereof.

14. An agent for dyeing keratinous fibers comprising at least two components, component (A) comprising in a medium suitable for dyeing said keratinous fibers an oxidation dye precursor and an aminoindole coupler, said aminoindole coupler having formula (I)

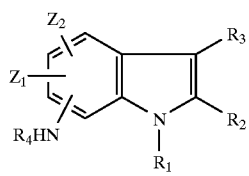

wherein $R_1$ represents hydrogen or a linear or branched $C_1$–$C_4$ alkyl, $R_2$ and $R_3$, each independently, represent hydrogen, $C_1$–$C_4$ alkyl or COOR' wherein R' represents $C_1$–$C_4$ alkyl or hydrogen, at least one of $R_2$ and $R_3$ represents hydrogen, $R_4$ represents hydrogen, $C_1$–$C_4$ alkyl, $C_1$–$C_4$ hydroxyalkyl, $C_2$–$C_4$ polyhydroxyalkyl or $C_1$–$C_6$ aminoalkyl wherein the amino function is optionally mono- or disubstituted by $C_1$–$C_4$ alkyl, the said —$NHR_4$ group occupying positions 4, 6 or 7, $Z_1$ and $Z_2$, each independently, represent hydrogen, $C_1$–$C_4$ alkyl, hydroxyl, halogen or $C_1$–$C_4$ alkoxy, at least one of said $Z_1$ and $Z_2$ being other than hydrogen, and a salt of said compound of formula (I), and component (B) comprising, in a medium suitable for dyeing said keratinous fibers, an oxidizing agent selected from the group consisting of hydrogen peroxide, urea peroxide and alkali metal bromates, the pH of components (A) and (B) being such that after mixing 90 to 10 percent of component (A) and 10 to 90 percent of said component (B), the resulting composition has a pH greater than 7.

15. The agent of claim 14 wherein said component (A) has a pH ranging from 8 to 12.

16. The agent of claim 14 wherein said component (A) contains an oxidation dye precursor and a coupler in an amount ranging from 0.05 to 7 percent by weight relative to the total weight of said component (A).

17. The agent of claim 14 wherein said aminoindole coupler of formula (I) is present in said component (A) in an amount ranging from 0.012 to 4 percent by weight based on the total weight of said component (A).

18. The agent of claim 14 wherein said component (A) contains a surface active agent present in an amount ranging from 0.1 to 55 weight percent; a solvent in addition to water in an amount ranging from 0.5 to 40 percent by weight, a thickening agent present in an amount ranging from 0.1 to 5 percent by weight and an antioxidant agent present in an amount ranging from 0.02 and 1.5 percent by weight.

* * * * *